US00PP20056P2

(12) United States Plant Patent
Danziger

(10) Patent No.: US PP20,056 P2
(45) Date of Patent: Jun. 2, 2009

(54) ***PETUNIA* PLANT NAMED 'DANLITTUN5'**

(50) Latin Name: *Petunia sensu Wijsman*
Varietal Denomination: Petunia

(76) Inventor: Gabriel Danziger, P.O. Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/157,174

(22) Filed: Jun. 6, 2008

(51) Int. Cl.
*A01H 5/00* (2006.01)

(52) U.S. Cl. ..... Plt./356
(58) Field of Classification Search ..... Plt./356
See application file for complete search history.

*Primary Examiner*—Annette H Para

(57) ABSTRACT

A new and distinct *Petunia* cultivar named 'DANLITTUN5' is disclosed, characterized by having white flowers with very slightly cream/green veins, small flowers and foliage a compact, mounded plant habit and continuous flowering. The new variety is a *Petunia*, normally produced as an outdoor garden or container plant.

2 Drawing Sheets

Latin name of the genus and species: *Petunia sensu Wijsman.*

BACKGROUND OF THE INVENTION

The new *Petunia* cultivar is a product of a planned breeding program conducted by the inventor, Gabriel Danziger, in Moshav Mishmar Hashiva, Israel. The objective of the breeding program was to produce *Petunia* varieties for commercial applications. The seed parent is the unpatented, proprietary seedling variety referred to as *Petunia* sensu Wijsman 'CV-690.' The pollen parent is the unpatented, proprietary seedling variety referred to as *Petunia sensu Wijsman* 'CV-74.' The new variety was discovered in April 2006 by the inventor in a group of seedlings resulting from that crossing, in a commercial greenhouse in Moshav Mishmar Hashiva, Israel.

Asexual reproduction of the new cultivar 'DANLITTUN5' by vegetative cuttings was first performed at a commercial greenhouse in Moshav Mishmar Hashiva, Israel in April 2006 and has shown that the unique features of this cultivar are stable and reproduced true to type in successive generations.

SUMMARY OF THE INVENTION

The cultivar 'DANLITTUN5' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANLITTUN5' These characteristics in combination distinguish 'DANLITTUN5' as a new and distinct *Petunia* cultivar:

1. Small flowers.
2. Compact growth habit.
3. Distinctive white flower coloration, with very moderate cream veins.
4. Suitability for outdoor containers and garden situations.

PARENT COMPARISON

Plants of the new cultivar 'DANLITTUN5' are similar to plants of the parent, *Petunia sensu Wijsman* 'CV 690' in most horticultural characteristics, however, plants of the new cultivar 'DANLITTUN5' have different color flowers.

Plants of the new cultivar 'DANLITTUN5' are similar to plants of the parent, *Petunia sensu Wijsman* 'CV-74' in most horticultural characteristics, however, plants of the new cultivar 'DANLITTUN5' have different color flowers.

COMMERCIAL COMPARISON

Plants of the new cultivar 'DANLITTUN3' are similar to plants of the commercial variety 'Danpetblu,' U.S. Plant Pat. No. 16,878 in most horticultural characteristics, however, plants of the new cultivar 'DANLITTUN3' have different flower coloration, smaller foliage and smaller diameter flowers.

Plants of the new cultivar 'DANLITTUN3' are also similar to plants of the commercial variety 'Danpetyel,' U.S. Plant Pat. No. 16,879 in most horticultural characteristics, however, plants of the new cultivar 'DANLITTUN3' have different flower coloration, smaller foliage and smaller diameter flowers.

BRIEF DESCRIPTION OF THE PHOTOGRAPH

Figure 1:
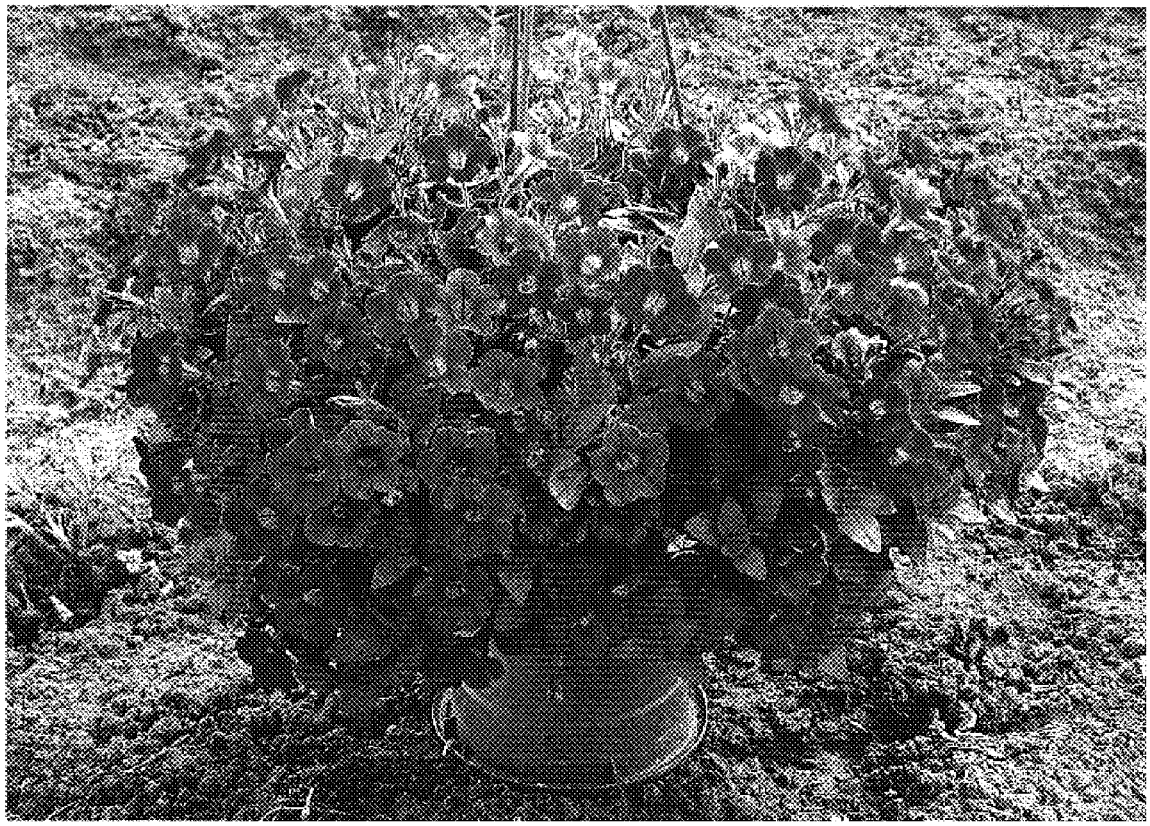

The accompanying photograph in FIG. 1 illustrates in full color a typical plant of 'DANLITTUN5' grown in a greenhouse, in a 16 cm basket. Age of the plant photographed is approximately 90 days from a rooted cutting.

Figure 2:
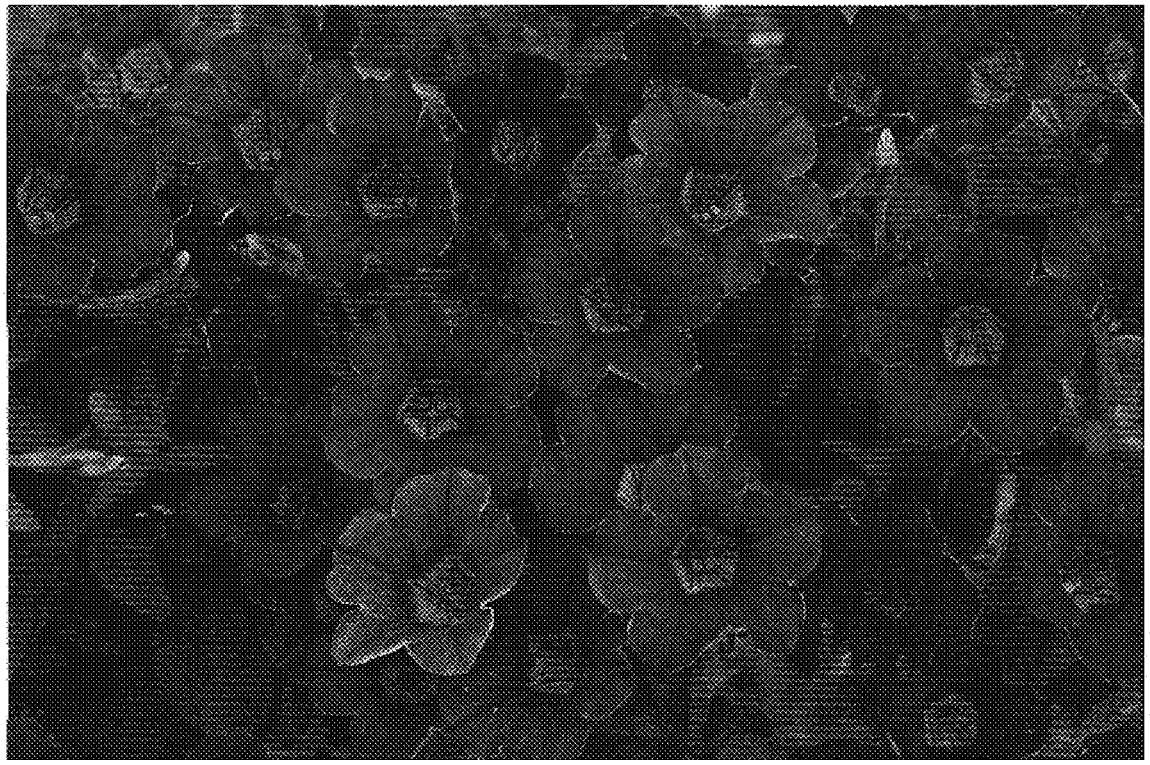

FIG. 2 illustrates in full color a close up of a typical bloom of 'DANLITTUN5.'

The photographs were taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Mini Colour Chart 2005, except where general terms of ordinary dictionary significance are used. The following observations and measurements describe 'DANLITTUN5' plants grown in a greenhouse in Moshav Mishmar Hashiva, Israel. The growing temperature ranged from 18° C. to 24° C. The greenhouse is subject to partial shade. General light conditions are bright, normal sunlight, with some shade during the brightest part of the day. Measurements and numerical values represent averages of typical plant types.

Botanical classification: *Petunia sensu Wijsman* cultivar 'DANLITTUN5.'

PROPAGATION

Time to initiate roots: About 8 days at approximately 18–30° C.
Time to develop roots: About 14–21 days at approximately 18–30° C.
Root description: Fine, fibrous.
Time to produce a rooted cutting: About 14 to 21 days at 18–30° C.

PLANT

Growth habit: Compact, spreading annual.
Pot size of plant described: 12 cm.
Age of plant described: Approximately 90 days from a rooted cutting.
Height:
*To top of flowers.*—Approximately 25–30 cm.
Plant spread: Approximately 50 cm.
Growth rate: Moderate.
Branching characteristics: Well-branched. Branches from base of plant.
Characteristics of lateral branches:
*Diameter.*—Approximately 0.2–3 cm
*Form.*—Cylindrical.
*Color.*—Near RHS Yellow-Green 144A.
*Texture.*—Smooth.
Internode length: Approximately 2 cm.

FOLIAGE

Leaf:
*Arrangement.*—Alternate.
*Quantity.*—Approximately 180 per branch.
*Average length.*—Approximately 3 cm.
*Average width.*—Approximately 1.5 cm.
*Shape of blade.*—Elliptic.
*Apex.*—Obtuse
*Base.*—Acute.
*Margin.*—Entire.
*Texture of top surface.*—Lustrous.
*Aspect.*—Slanted upward 45–90°.
*Color.*—Young foliage upper side: Near RHS Yellow-Green 146A. Young foliage under side: Near RHS Yellow-Green 146A. Mature foliage upper side: Near RHS Yellow-Green 147A. Mature foliage under side: Near RHS Yellow-Green 146A.
*Venation.*—Type. Pinnate. Venation color upper side: Near RHS Yellow-Green 144C. Venation color under side: Near RHS Yellow-Green 144C.
*Petiole.*—Length 0.5 cm. Diameter: 0.5 cm. Color: Near RHS Yellow-Green 144C.

FLOWER

Natural flowering season: Freely flowering all year in Moshav Mishmar Hashiva Israel. Begins flowering approximately 55 days after planting a rooted cutting.
Inflorescence and flower type and habit: Salverform, horizontal single with fused petals.
Rate of flower opening: Approximately 4 to 5 days from bud to fully opened flower.
Flower longevity on plant: Individual flowers last 4 to 5 days on the plant.
Quantity of flowers: Approximately 60 per plant.
Flower size:
*Diameter.*—Approximately 2.5 cm.
*Flower tube length.*—Approximately 2 cm.
*Flower tube diameter at distal end.*—Approximately 0.7 cm.
*Flower tube diameter at proximal end.*—Approximately 0.2 cm.
Petals:
*Length from throat.*—About 1 cm.
*Width.*—About 2 cm.
*Quantity.*—5, fused.
*Texture.*—Smooth
*Apex.*—Truncate.
*Margin.*—Entire
Color:
*When opening.*—Upper surface: Near RHS White N157D: Lower surface: Near RHS White N157D.
*Fully opened.*—Upper surface: Near RHS White N157D. Lower surface: Near RHS White N157D. Flower throat (inside): Near RHS White N157D. Flower throat, vein: Near RHS Green 142C. Flower tube (outside): Near RHS Green 142D. Flower tube, vein: Near RHS Green 142C. Petal color, fading to: Does not fade.
Bud:
*Shape.*—Ovate.
*Length.*—Approximately 0.5 cm.
*Diameter.*—Approximately 0.25 cm.
*Color.*—Near RHS Green 142C.
Calyx/Sepals:
*Quantity per flower.*—5, fused at base.
*Sepal shape.*—Oblong.
*Length.*—Approximately 1 cm.
*Width.*—Approximately 0.2 cm.
*Apex.*—Obtuse.
*Base.*—Fused.
*Margin.*—Entire.
*Texture.*—Pubescent.
*Color.*—Upper Surface: Near RHS Green 137A. Lower Surface: Near RHS Green 137B.
Peduncle:
*Length.*—Approximately 2 cm.
*Diameter.*—Approximately 0.1 cm.
*Color.*—Near RHS Green 137B.
*Orientation.*—Upright.
Fragrance: None.

REPRODUCTIVE ORGANS

Stamens:
*Number.*—5.
*Filament length.*—Approximately 1.5 cm.
Anthers:
*Length.*—Approximately 0.1 cm.
*Shape.*—Oblate.

*Color.*—Near RHS White 155A.

*Pollen.*—Color: Near RHS White 155A. Quantity: Abundant.

Pistil:

*Number.*—1.

*Length.*—Approximately 1.5 cm.

*Style.*—Length: Approximately 0.1 cm. Color: Near RHS Yellow-Green 146C.

*Stigma.*—Shape: Oblate. Color: Near RHS Yellow-Green 146C. Ovary Color: Near RHS Yellow-Green 146C.

OTHER CHARACTERISTICS

Seeds and fruits: Produces a moderate amount of seeds compared to similar commercial petunias.

Disease/pest resistance: Neither resistance nor susceptibility to pathogens and pests common to *Petunia* have been observed.

Temperature tolerance: The new variety tolerates temperatures between 8 to 35° C.

What is claimed is:

1. A new and distinct cultivar of *Petunia* plant named 'DANLITTUN5' as herein illustrated and described.

* * * * *